United States Patent [19]
Norton

[11] Patent Number: 5,870,886
[45] Date of Patent: Feb. 16, 1999

[54] TRANSFER SYSTEM FOR TRANSFERRING OBJECTS INTO A BARRIER ISOLATOR

[75] Inventor: Paul H. Norton, Trumbauersville, Pa.

[73] Assignee: The West Company, Incorporated, Lionville, Pa.

[21] Appl. No.: 948,183

[22] Filed: Oct. 9, 1997

Related U.S. Application Data

[63] Continuation-in-part of Ser. No. 794,029, Feb. 3, 1997, Pat. No. 5,715,659.
[51] Int. Cl.$^6$ ..................................................... B65B 55/00
[52] U.S. Cl. .............................. 53/492; 53/167; 53/381.2; 53/468; 414/292; 414/412; 312/1; 312/296
[58] Field of Search .................................... 83/946; 312/1, 312/296; 53/167, 381.2, 425, 426, 492, 468; 156/251, 515; 141/85, 93, 97; 414/292, 403, 412

[56] References Cited

U.S. PATENT DOCUMENTS

| | | |
|---|---|---|
| 3,016,284 | 1/1962 | Trexler . |
| 3,289,698 | 12/1966 | Cazalis et al. . |
| 3,893,578 | 7/1975 | Melton et al. . |
| 4,253,500 | 3/1981 | Williams ............................... 53/468 X |
| 4,724,874 | 2/1988 | Parikh et al. . |
| 4,805,378 | 2/1989 | Anderson . |
| 4,916,885 | 4/1990 | Loliger . |
| 4,991,633 | 2/1991 | Wong . |
| 5,117,875 | 6/1992 | Marrucchi . |
| 5,257,957 | 11/1993 | Diccianni et al. . |
| 5,259,812 | 11/1993 | Kleinsek . |
| 5,275,479 | 1/1994 | Cruz et al. . |
| 5,291,925 | 3/1994 | Marrucchi ............................. 53/468 X |
| 5,425,793 | 6/1995 | Mori et al. . |
| 5,447,699 | 9/1995 | Papciak et al. . |
| 5,460,439 | 10/1995 | Jennrich et al. . |
| 5,567,025 | 10/1996 | Haag . |
| 5,715,646 | 2/1998 | Smekens . |

*Primary Examiner*—Daniel Moon
*Attorney, Agent, or Firm*—Panitch Schwarze Jacobs & Nadel, P.C.

[57] ABSTRACT

A transfer system for transferring objects into a barrier isolator is provided. The barrier isolator includes a barrier wall to maintain a decontaminated environment in an isolated space. The transfer system includes a port opening located in the barrier wall. A first port barrier film is sealingly located over the port opening. A container is provided which includes an interior cavity which contains a second, replacement port barrier film and which is adapted to further receive and hold decontaminated objects to be delivered through the port opening and into the isolated space. A container barrier film is sealingly connected to the container to seal the second, replacement port barrier film and the decontaminated objects within the cavity in a decontaminated state. The container barrier film has a first, decontaminated side which faces the cavity, and a second exposed side, positionable adjacent to the port barrier film. A parting and sealing element is located within the isolated space and is adapted to part the first port barrier film and the container barrier film to define a transfer opening in the first port and container barrier films and to simultaneously seal together and decontaminate the edges of the first port and container barrier films such that the exposed and potentially contaminated second sides of the first port barrier film and the container barrier film are locked together and remain isolated from the isolated space allowing the decontaminated objects and the second, replacement port barrier film to be passed into the isolated space.

11 Claims, 8 Drawing Sheets

TRANSFER SYSTEM FOR TRANSFERRING OBJECTS INTO A BARRIER ISOLATOR

CROSS-REFERENCE TO RELATED APPLICATIONS

This application is a continuation-in-part of U.S. patent application Ser. No. 08/794,029, filed on Feb. 3, 1997, now U.S. Pat. No. 5,715,659.

BACKGROUND OF THE INVENTION

The present invention relates to isolated rooms and/or equipment for maintaining an aseptic environment, and in particular, to a system for transferring sterile objects into such an isolated space.

In the past, the production and handling of certain products, such as pharmaceuticals, was carried out in a clean room in order to avoid contamination of the product during processing. The clean room was maintained as an isolated, aseptic area and equipment or other objects entering the isolated area, such as consumables used during the processing of such products, had to be sterilized prior to being introduced into the aseptic environment. Additionally, personnel working in such rooms were required to wear protective clothing to prevent contamination of the area.

Recently, in order to reduce the expenses associated with operating a clean room, barrier-isolated equipment has been introduced which maintains a local aseptic environment directly around processing equipment for certain types of products. The equipment is accessed through glove portals and objects are sterilized and transferred into the isolated area via air locks. The objects being introduced into the isolated area can be presterilized or are sterilized within the air lock prior to being introduced into the barrier isolated area. Generally, each machine or isolated area would require an air lock or treatment vessel which receives the articles to be sterilized, such as closure elements for pharmaceutical containers. The closure elements are then sterilized within the treatment vessel prior to being passed into the isolated system.

It would be desirable to reduce the time required and cost involved for sterilizing parts or other materials which are to be introduced into an isolated system on site.

One solution to this problem, which is described in U.S. Pat. No. 5,447,699, which was jointly invented by the present inventor and is assigned to the assignee of the present invention, provides a combination container for holding sterilized elements such as vial stoppers and a sterilizable transfer port for transferring the sterilized elements into the isolation system. However, exposed areas of the transfer port components must still be sterilized on site prior to the transfer of elements into the isolation system. This arrangement allows the required elements to be sterilized at a different location prior to shipping to the processing and packaging company where the sterilized elements are fed into the isolation system, such as a system for bottling pharmaceuticals.

BRIEF SUMMARY OF THE INVENTION

Briefly stated, the present invention provides a transfer system for transferring objects into a barrier isolator. The barrier isolator includes a barrier wall to maintain a decontaminated environment in an isolated space. The transfer system includes a port opening located in the barrier wall to provide access to the isolated space. A first port barrier film is sealingly located over the port opening. The first port barrier film has a first, decontaminated side which faces the isolated space and a second side which faces away from the isolated space. A container is provided which includes an interior cavity which contains a second, replacement port barrier film and which is adapted to further receive and hold decontaminated objects to be delivered through the port opening and into the isolated space. A container barrier film is sealingly connected to the container to seal the second, replacement port barrier film and the decontaminated objects within the cavity in a decontaminated state. The container barrier film has a first, decontaminated side which faces the cavity, and a second exposed side, positionable adjacent to the port barrier film. A parting and sealing element is located within the isolated space adjacent to the port opening, and is mounted for movement to an in-use position adjacent to the first side of the first port barrier film. The parting and sealing element is adapted to part the first port barrier film and the container barrier film to define a transfer opening having edges in the first port barrier film and the container barrier film and to simultaneously seal together and decontaminate the edges of the first port barrier film and the container barrier film such that the exposed and potentially contaminated second sides of the first port barrier film and the container barrier film are locked together and remain isolated from the isolated space. This allows the decontaminated objects and the second, replacement port barrier film to be passed from the container cavity, through the transfer opening and into the isolated space while maintaining the decontaminated environment.

In another aspect, the present invention provides a container for use in a transfer system for transferring objects into a barrier isolator which includes a barrier wall to maintain a decontaminated environment in an isolated space. The barrier isolator has a port opening with a first port barrier film which seals the port opening. The container includes a plurality of walls defining an interior cavity with an opening. A second, replacement port barrier film is located in the cavity. The interior cavity is further adapted to hold objects to be delivered with the second, replacement port barrier film through the port opening and into the isolated space. A container barrier film is sealingly connected to the container to seal the cavity.

In another aspect, the present invention provides a method of supplying decontaminated objects and a replacement port barrier film to a decontaminated environment in an isolated space delimited by a barrier wall. The method includes the steps of:

(a) providing a port opening in the barrier wall and a first port barrier film sealing the port opening, the first port barrier film having a first, decontaminated side facing the isolated space to close-off the isolated space and a second, exposed side;

(b) positioning a container adjacent to the port opening, the container having a decontaminated interior cavity with decontaminated objects and a second, replacement port barrier film sealed within the cavity by a container barrier film, the container barrier film having a first decontaminated side and a second, exposed side, the second side of the first port barrier film being in facing engagement with the second side of the container barrier film;

(c) simultaneously creating a transfer opening in the first port barrier film and the container barrier film and sealing together edges formed around the transfer opening in the first port barrier film and the container barrier film with a parting and sealing element located inside the isolated space;

(d) transferring the decontaminated objects and the second, replacement port barrier film from the container, through the transfer opening in the first port barrier film and the container barrier film, and into the isolated space; and (e) resealing the port opening with the second, replacement port barrier film while maintaining the decontaminated environment in the isolated space.

BRIEF DESCRIPTION OF SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the transfer systems in accordance with the present invention for transferring objects into a barrier isolator 12 and designated parts thereof. The terminology includes the words above specifically mentioned, derivatives thereof and words of similar import.

Referring to the drawings, wherein like numerals indicate like elements throughout, there is shown in FIG. 1(a)–FIG. 1(f) the transfer system 10 for transferring objects 14 into a barrier isolator 12. In the preferred embodiment, the barrier isolator 12 is used to enclose equipment used in bottling pharmaceutical products in an aseptic environment, and preferably, the objects 14 are vial stoppers which are directed by a chute 16 into a hopper 18 which feeds the stoppers to the bottling equipment.

Figure 1A:
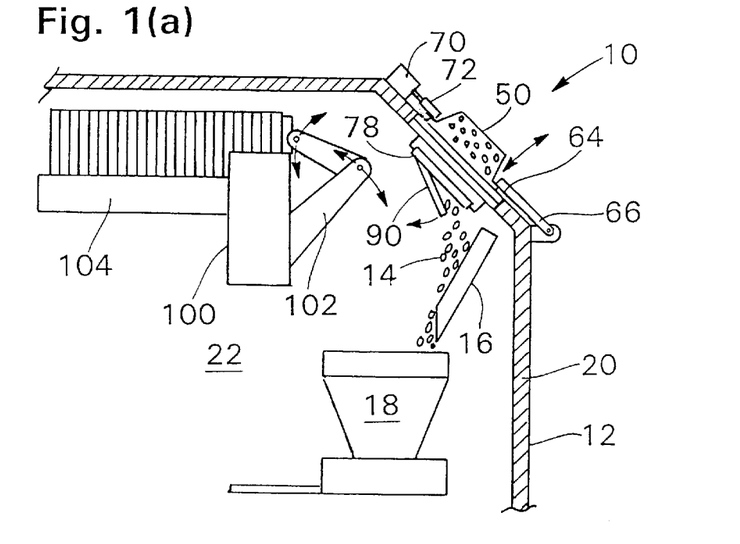
FIG. 1(a)–FIG. 1(f) are sequential side elevational views showing the operation of a transfer system for transferring objects into a barrier isolator in accordance with a first embodiment of the present invention.

The barrier isolator 12 includes a barrier wall 20, most completely illustrated in cross-section in FIG. 1(a), which maintains a decontaminated environment in an isolated space 22 enclosed by the barrier wall 20. The barrier wall 20 is preferably made of an impermeable material and may be sized to enclose a piece of equipment or an entire production line depending upon the particular application. For the purposes of the present application, the barrier wall 20 is meant to refer to any dividing member used to isolate an enclosed space.

Figure 2:
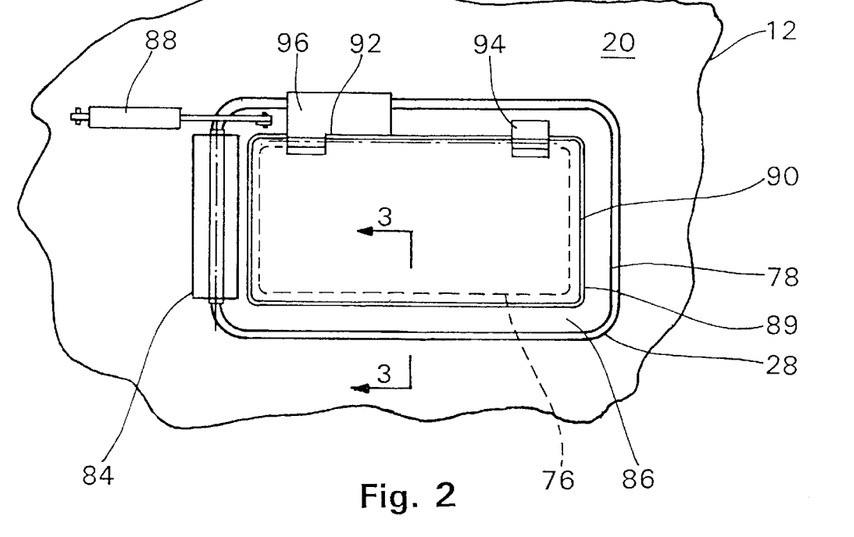
FIG. 2 is a view taken along line 2—2 of FIG. 1(f)

Referring now to FIG. 2, a port opening 28 is located in the barrier wall 20 to provide access to the isolated space 22. Preferably, the port opening 28 is surrounded by a reinforcement 30 shown in greater detail in FIG. 3, which extends around an opening 32 in the barrier wall 20. The reinforcement 30 has a surface 34 which surrounds the port opening 28 and a predetermined depth. Preferably, a plurality of spaced apart annular seals 36 which surround the port opening 28 are located on the surface 34. Preferably, the annular seals 36 are located in the dovetail grooves 38 in the surface 34 of the reinforcement 30. In the preferred embodiment, at least two annular seals 36 are provided, and more preferably four annular seals are used. However, it will recognized by those skilled in the art from the present disclosure that the reinforcement 30 could be formed integrally with the barrier wall 20, and need not be a separate part attached in an opening in the barrier wall 20.

Figures 3, 6:
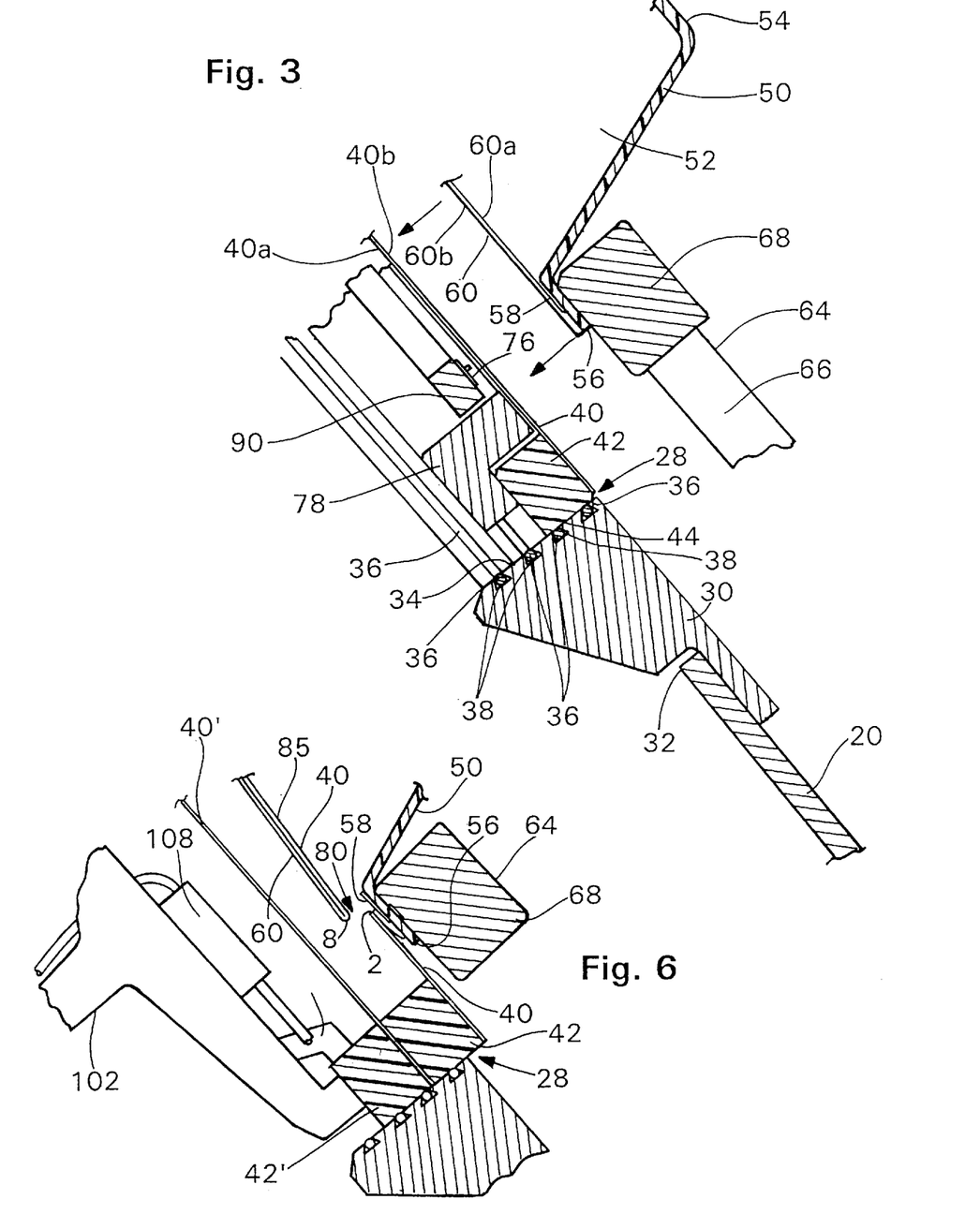
FIG. 3 is an enlarged cross-sectional view taken along line 3—3 in FIG. 2 showing a container being positioned adjacent to the port opening for transferring objects into the barrier isolator.
FIG. 6 is a cross-sectional view similar to FIG. 3 showing the installation of a next port barrier into the port opening.

The annular seals 36 are preferably round in cross section, and protrude above the surface 34 from the dovetail grooves 38. However, it will be recognized by those skilled in the art from the present disclosure that other types of seals could be used, if desired, such as a flap or wiper seals mounted directly to the surface 34 of the reinforcement 30.

Referring to FIG. 3, a port barrier film 40 is sealingly located over the port opening 28. The port barrier film 40 has a first, decontaminated side 40a which faces the isolated space 22 and a second side 40b which is exposed. Preferably, the port barrier film 40 is mounted in a frame 42 having an outer periphery 44 which is complementary and designed for a minimal clearance fit with the port opening 28. The outer periphery 44 of the frame 42 is sealingly engaged by at least one annular seal 36. The frame 42 is also slidably displacable through the port opening 28 along the surface 34 while maintaining sealed contact around the entire outer periphery of the frame 42 with one or more of the annular seals 36.

In the preferred embodiment, the frame 42 is made of a polymeric material, such as polyethylene. However, it will be understood that the frame can be made from a metallic material or any other suitable impermeable material, if desired. Each frame 42 has a thickness to provide a desired rigidity, and the thickness is preferably 0.5 inches or greater. Preferably, the depth of the reinforcement surface 34 is greater than the thickness of two frames 42 such that a first frame 42 can be displaced outwardly from the opening while a second frame 42' is sealingly engaged by at least one annular seal 36 in the port opening 28 to maintain isolation of the isolated space 22 as the frame 42 is removed, as shown in detail in FIG. 6, which will be explained in more detail below.

Referring to FIGS. 1(*a*) and 3, a container 50 which is adapted to hold the objects 14 to be delivered through the port opening 28 and into the isolated space 22 is provided. As shown in FIG. 3, the container 50 includes an interior cavity 52 adapted to receive decontaminated objects 14, and a flange 56 which extends outwardly around the opening to the interior cavity 52. The container exterior 54 is exposed in use. Preferably, the container 50 is made of a single piece of thermoformed polymeric material, and the flange 56 is integrally formed with the container 50. However, it will be recognized by those skilled in the art from the present disclosure that other materials can be used to made the container 50 and that the container 50 could be made from more than one piece of material, if desired.

Still with reference to FIG. 3, in the first embodiment, a shield 58 is located on an inner periphery of the flange 56 of the container 50 to prevent the parting and sealing element 76 from acting on the flange 56, as explained in detail below. The shield 58 is preferably a thin sheet of heat resistant material, such as aluminum foil or other metallic foil which is attached to the surface of the flange 56. However, it will be recognized by those skilled in the art from the present disclosure that the shield 58 can be omitted if the flange 56 itself is made of a suitable heat resistant material.

A container barrier film 60 is engaged to an outer periphery of the flange 56 such that the decontaminated objects 14 are adapted to be sealed within the interior cavity 52 in the container 50 and remain decontaminated in the cavity 52. The container barrier film 60 has a first, decontaminated side 60*a* which faces the cavity 52, and a second exposed side 60*b* which is exposed to outside air.

Preferably, both the port and container barrier films 40 and 60 are made of a polymeric material such as polyethylene having a thickness of approximately 0.004 inches. The container barrier film 60 is preferably connected to the flange 56 by an adhesive or a heat sealed connection between the outer most periphery of the container barrier film 60 and the flange 56. No connection is provided between the container barrier film 60 and the shield 58, and the barrier film 60 is releasable from the shield 58. The port barrier film 40 is attached to the port frame 42 in a similar manner.

Referring now to FIGS. 1(*a*)–1(*f*) and FIG. 3, a holder 64 is located adjacent to the port opening 28. The holder 64 preferably includes a hinged arm 66 which is connected to a support frame 68 having an opening defined therethrough for receiving the container 50, with the flange 56 of the container 50 being supported on the frame 68. A latching mechanism 70, shown in FIGS. 1(*a*)–1(*f*), is attached to the outside of the barrier isolator 12 and includes a movable latch element which contacts the support frame 68 to lock the container 50 in position adjacent to the port opening 28, with the second side 40*b* of the port barrier film 40 being in facing engagement with the second side 60*b* of the container barrier film 60. Preferably, the latching mechanism 70 includes an solenoid actuated latch 72 which is adapted to engage the container holder frame 68 to hold the container holder 64 in position. Solenoid actuated mechanisms which are used as latching elements are generally known in the art. Accordingly, further description is not believed to be necessary. It will be recognized by those skilled in the art from the present disclosure that any type of latching mechanism, such as a manually engaged latch, can be used, if desired, to hold the container holder 64 with the container 50 in position. It will be similarly recognized that the latching mechanism 70 may be omitted depending upon the configuration and position of the container holder 64 and the container 50. For example, if the combined weight of the container holder 64 and container 50 is sufficient to maintain the container 50 in position.

Figure 4:
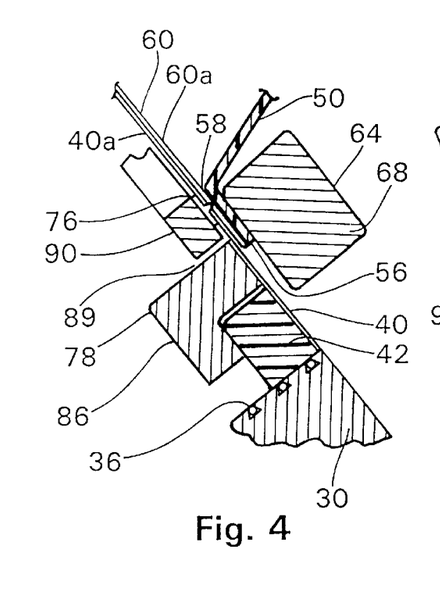
FIG. 4 is an enlarged cross-sectional view similar to FIG. 3 showing the parting and sealing element forming an opening in the barrier films.
Figure 5:
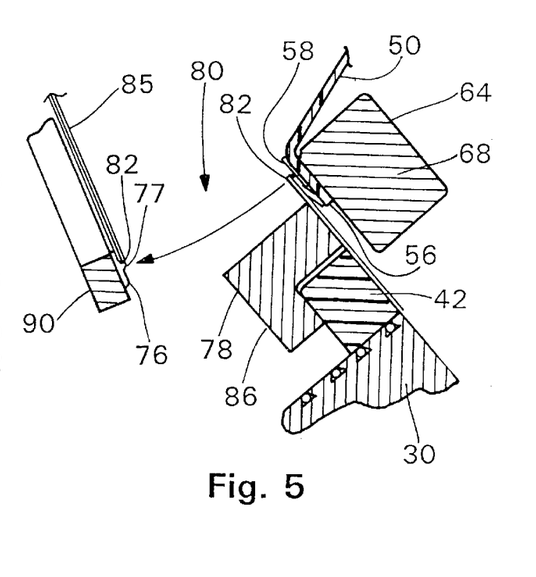
FIG. 5 is an enlarged cross-sectional view similar to FIG. 3 showing the container opening for transferring objects into the barrier isolator.

Referring now to FIGS. 1(*b*), 1(*f*), 2 and 4, a parting and sealing element 76 is located within the isolated space 22 adjacent to the port opening 28. The parting and sealing element 76 is mounted for on a door assembly 78 for movement from a first position, shown in FIG. 1(*b*), to a second, in-use position adjacent to the first side 40*a* of the port barrier film 40, as shown in FIGS. 1(*f*), 3 and 4. The parting and sealing element 76 is used to part the port and container barrier films 40 and 60 as shown in FIG. 5 to define a transfer opening 80 having edges 82 in the port and container barrier films 40 and 60. The parting and sealing element 76 is used to simultaneously seal together and decontaminate the edges 82 of the port and barrier films 40 and 60 such that the exposed and potentially contaminated second sides 40*b*, 60*b* of the port and container barrier films 40, 60 are locked together and remain isolated from the isolated space 22. Preferably, the parting and sealing element 76 is aligned with the shield 58 covered area of the flange 56, as shown in FIG. 4. The shield 58 is located on the flange to prevent the barrier films 40, 60 from adhering to a portion of the flange 56 during the parting and sealing operation.

Figure 8:
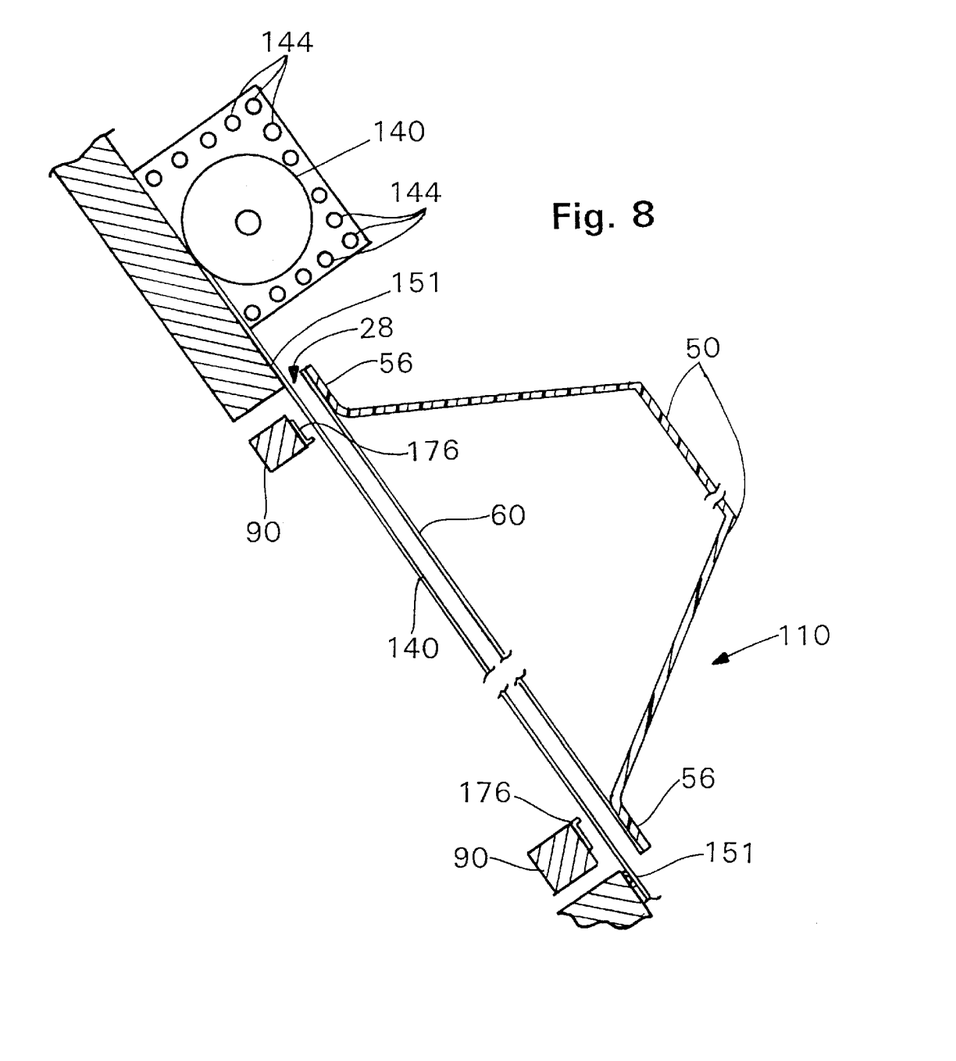
FIG. 8 is a cross-sectional view taken along line 8—8 in FIG. 7.

It is also possible to align the parting and sealing element 76 along an inside edge of the flange 56, as shown in FIG. 8 in connection with the second embodiment of the invention, while using an external member (not shown) to apply external pressure to the container 50 for support during the parting of the barrier films 40, 60 while simultaneously sealing together and decontaminating the edges. In this case, the shield 58 is also not required.

As shown in detail in FIG. 5, preferably the parting and sealing element 76 is a heating element having a raised portion 77 which is used to simultaneously part the barrier films 40,60, seal the edges 82 together, and decontaminate the edges 82 around the opening 80 to ensure that the isolated space is not contaminated. One preferred heating element is available from Toss Machine Components of Nazareth, Pa.

As best shown in FIG. 2, the parting and sealing element 76 extends around at least two, and preferably three sides of the flange 56 of the container 50, and is adapted to form a flap 85 from the port and container barrier films 40, 60. The edges 82 along both the flap 85 and the opening 80 are simultaneously sealed and decontaminated by the parting and sealing element 76.

Referring now to FIG. 2, the door assembly 78 is preferably connected to the wall 20 of the barrier isolator by hinge 84 which allows the door assembly 78 to be swung from a closed position, as shown in FIG. 1(*f*) to an open position as shown in FIG. 1(*b*). As shown in FIGS. 2 and 4, the door assembly 78 includes an outer door frame 86 to which the first hinge 84 is connected. Preferably, an actuator 88 is connected between the barrier wall 20 and the outer frame 86 to open and close the door. The actuator 88 can be electrically or pneumatically operated, preferably from a remote location outside of the isolated space 22. An opening 89 is provided in the outer door frame 86, and an inner door 90 is located in the opening 89. The inner door 90 is supported by hinges 92, 94. Preferably, an actuator 96 is provided for moving the inner door 90 relative to the outer door frame 86, as shown in FIG. 1(a). The parting and sealing element 76 is supported by the inner door 90. The inner door 90 also acts a support for the flap 85, which is movable between a first position, as shown in FIGS. 1(f) and 4, in which the inner door 90 is adapted to engage the flap 85 and hold the flap 85 in a closed position, and a second position as shown in FIGS. 1(a) and 5 in which the inner door moves away from the port opening 28, allowing the flap 85 to open.

Referring now to FIGS. 1(a)–1(f), once the sterilized objects 14 are transferred from the container into the isolated space 22, a new port frame 42' with an uncut barrier film 40 is placed in the port opening 28 from inside the barrier isolator 12, and is sealingly engaged by annular seals 36 adjacent to the inner edge of the reinforcement 30.

Preferably a robot 100 with an arm 102 is used to load new port barrier frames 42' into the port opening 28. In FIG. 1(a), the arm 102 is shown in position to pick up a next port barrier frame from a magazine 104 which holds additional frames 42 located inside the barrier isolator 12. Referring to FIG. 6, preferably at least one solenoid actuated clamp 106 is mounted on the end of the robotic arm 102 for gripping the port barrier frame 42. Preferably, at least two clamps 106 are attached to the arm 102 and are moved inwardly or outwardly by an actuator 108 in order to grip the port barrier frame 42. It will recognized by those skilled in the art from the present disclosure that other types of holding mechanisms could be provided on the end of the robotic arm 102 in order to grip port barrier frames 42 to remove them from the magazine 104 and move them into position in the port opening 28, and the present invention is not limited to the type of mechanism used.

Figure 1B:
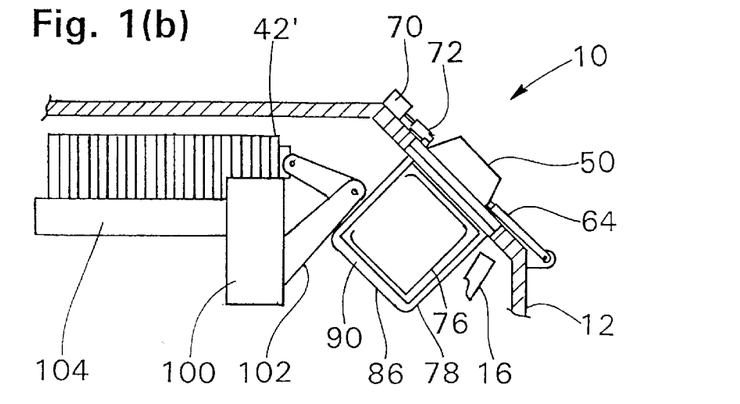
Figure 1C:
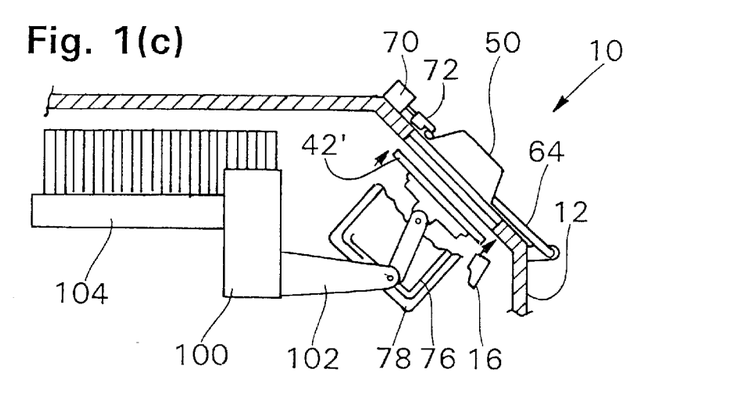

Once the container 50 has been emptied as shown in FIG. 1(b), the inner door 90 is closed and the outer door frame 86 is opened by the actuator 88 to move the door assembly 78 away from the port opening 28. As shown in FIGS. 1(b) and 1(c), the arm 102 is used to remove the next port barrier frame 42' from the magazine 104 and insert the next frame 42' into port opening 28.

As shown in detail in FIG. 6, the next port barrier frame 42' is used displace the first port barrier frame 42 with the attached container 50 out of the port opening 28. The annular seals 36 preventing contamination of the isolated space 22. Preferably, a positive pressure is also maintained within the isolated space 22 to ensure that there is an outflow of air from within the isolated space 22 through any gaps which may form during the insertion of the next port frame 42'.

Figure 1D:
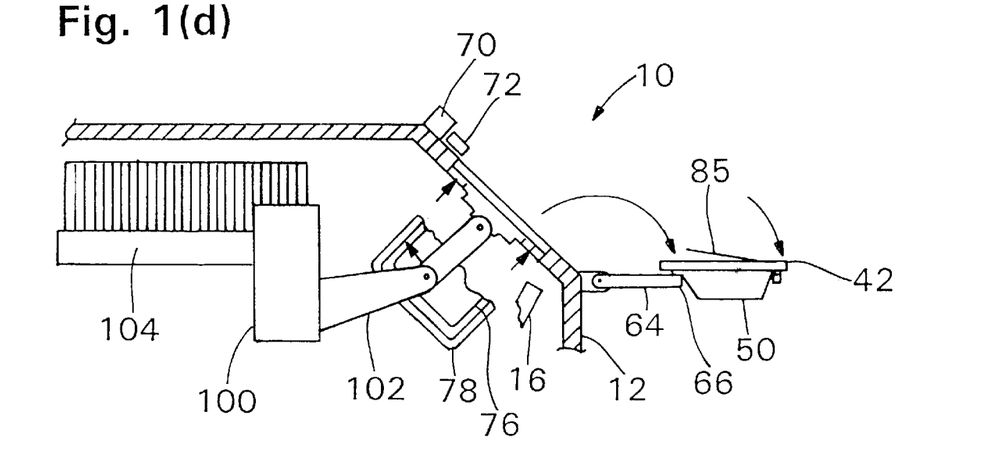
Figure 1E:
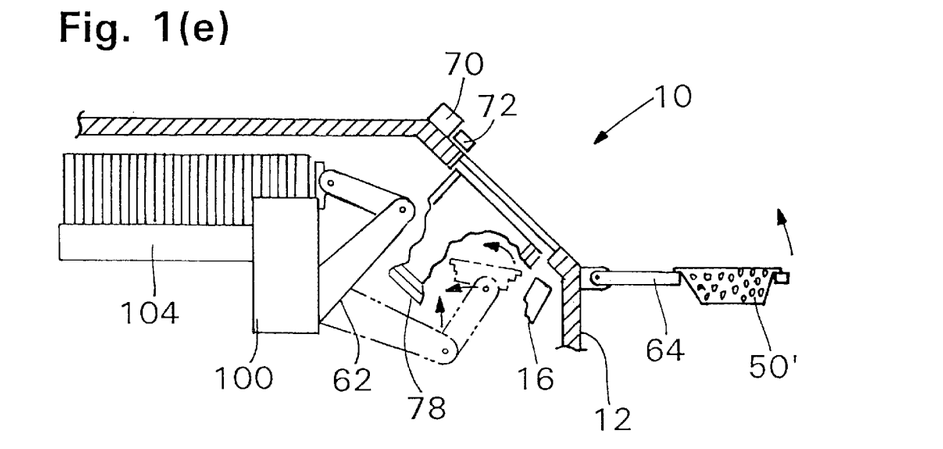

As shown in FIG. 1(d), once the next port barrier frame 42' is in position, the latching mechanism 70 is released such that the hinged arm 66 can be opened and the empty container 50 with the attached port and container barrier films 40 and 60 can be removed and disposed. As the arm 102 is moved back to its starting position, a new container 50' filled with sterilized objects to be transferred into the barrier isolator 12 can be loaded in the container holder 64, as shown in FIG. 1(e).

Figure 1F:
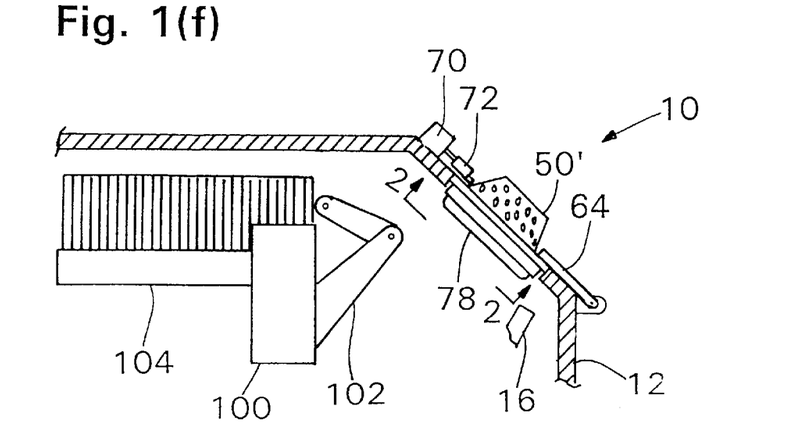

Decontaminated objects 14 are supplied to the decontaminated environment in the isolated space 22 as described above, by clamping the container 50 or 50' to the port opening 28. As shown in FIGS. 1(f) and 3, the container 50' or 50 is clamped in position by the latching mechanism 70, which holds the container holder 64 in position with the second side 60b of the container barrier film 60 located in facing engagement with the second side 40b of the port barrier film. The door assembly 78 is moved from the first position, shown most clearly in FIGS. 1(b) and 1(e), to the second position, shown in FIG. 1(f), to position the parting and sealing element 76 adjacent to the first surface 40a of the port barrier film 40, as shown in FIG. 4. Energy is supplied to the parting and sealing element 76 and pressure is applied by the inner door 90 such that the parting and sealing heating 76 simultaneously creates an opening 80 in the port and container barrier films 40, 60 and seals together the edges 82 formed around the opening 80 in the port and container barrier films 40, 60. The inner door 90 is then pivoted outwardly away from the barrier isolator wall 20 as shown in FIG. 1(a) and acts as a support for the flap 85 created by the parting and sealing element 76, as shown in FIG. 5. The inner door 90 is used to position the flap 85 for controlled discharge and transfer of the decontaminated objects 14 from within the container 50 through the transfer opening 80 in the port and barrier films 40 and 60, and into the isolated space 22. The isolated space 22 within the barrier isolator 12 remains uncontaminated during transfer since the edges 82 around the opening 80 in the port and container barrier films 40 and 60 are sealed together. Once the contents of the container 50 have been transferred, the inner door 90 is closed, and the outer door frame 86 is opened inwardly, and the process is repeated.

Figure 7:
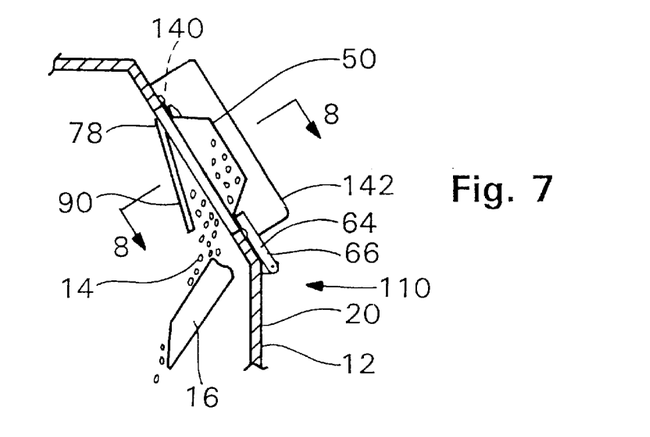
FIG. 7 is a partial elevational view similar to FIG. 1(a) illustrating a second embodiment of a transfer system for transferring objects into a barrier isolator.

Referring now to FIG. 7, a second embodiment of a transfer system 110 in accordance with the present invention is shown. The second embodiment 110 is similar to the first embodiment, except that the port barrier film is provided as a pre-sterilized roll 140 of material which is dispensed across the port opening 28. As shown in FIGS. 7 and 8, the pre-sterilized roll of barrier film 140 is rotatably supported in a microbial kill housing 142 located adjacent to the port opening 28. Preferably, the microbial kill housing 142 is a heat box having heating elements 144 located therein adjacent to the pre-sterilized roll of barrier film 140.

The port barrier film 140 is slidably movable across the port opening 28 and seals 151 are provided around the entire outer periphery of the port opening 28 which engage at least one surface of the port barrier film 140. The port and container barrier films 140, 60, are parted and sealed by the parting and sealing element 176, which is similar to the parting and sealing element 76 described in connection with the first embodiment, in the same manner as previously described. However, the raised portion 177 of the parting and sealing element 176 is aligned along an inside edge of the flange 56 so that the shield 58 is not required.

In order to remove the empty container 50 with the attached port barrier film 140, the empty container 50 with the attached port barrier film is slidably displaced until the entire container 50 passes beyond the port opening 28 while additional barrier film material 140 is drawn from the roll across the port opening 28. The seals 151 prevent contaminants from entering through the port opening 28.

While heat is the preferred mode of operation for the parting and sealing element 76 for parting and sealing the barrier films 40, 60, 140, other modes may be used, if desired. For example, ultrasonic welding and cutting can be used to part and seal the barrier films. It may be desirable or necessary in some of the alternative modes to provide supplemental sterilization at the cut edges, such as through the use of UV light, germicides, etc.

Referring now to FIGS. 9(a)–9(e) and 10–12, a third embodiment 210 of a transfer system for transferring objects into a barrier isolator 212 is shown. The third embodiment is similar to the first embodiment and like elements have been identified with similar reference numerals which are 200 greater than the reference numerals from the first embodiment 10. For example, the container 250 in accordance with the third embodiment of the transfer system 210 is similar to the container 50 in accordance with the first preferred embodiment of the invention 10. Accordingly, a detailed description of these similar features has been omitted, and a description of the differences between the first and third embodiments 10, 210 are described in detail below.

As shown in FIGS. 9(a)–9(e), a port opening 228 is located in the barrier wall 220 to provide access to the isolated space 222. A first port barrier film 240, which is preferably mounted on a frame 242, is sealingly located in the port opening 228. As in the first embodiment, the first port barrier film 228 has a first, decontaminated side 240a which faces the isolated space 222, and a second side 240b which faces away from the isolated space 222, and is exposed. A similar system of annular seals 236 located on a surface 234 of the port opening 228 are utilized to form a seal against the frame 242.

Figure 9A:
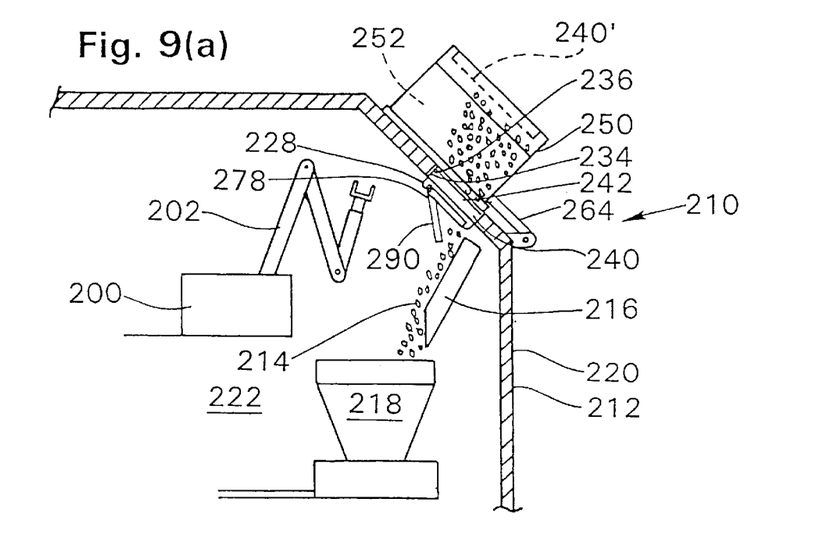
FIGS. 9(a)–9(e) are sequential side elevational views showing the operation of a third embodiment of a transfer system for transferring objects into a barrier isolator in accordance with the present invention.
Figure 9B:
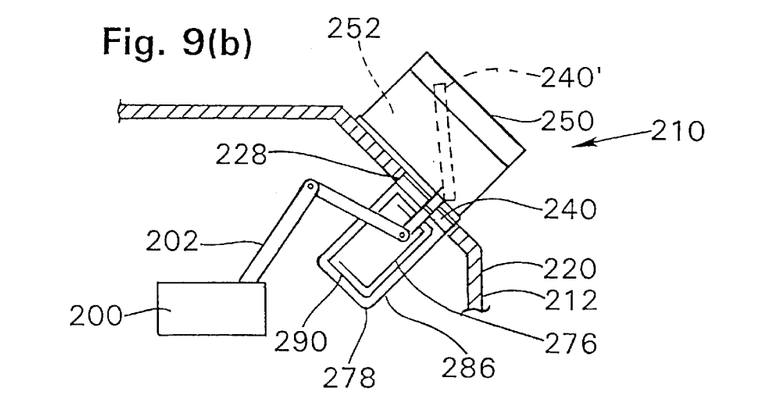
Figure 9C:
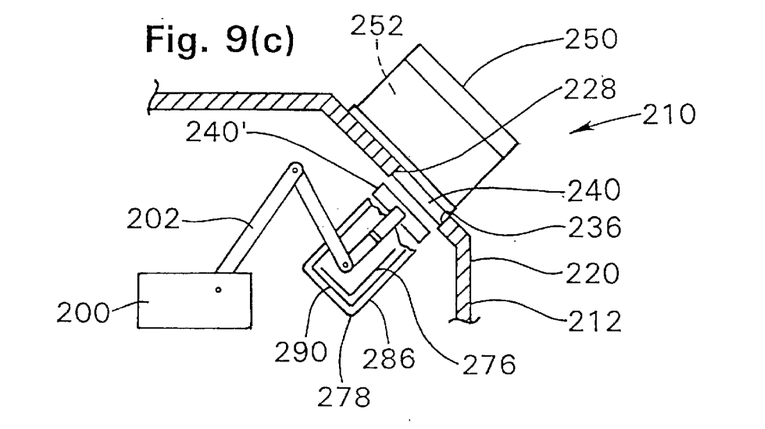
Figure 9D:
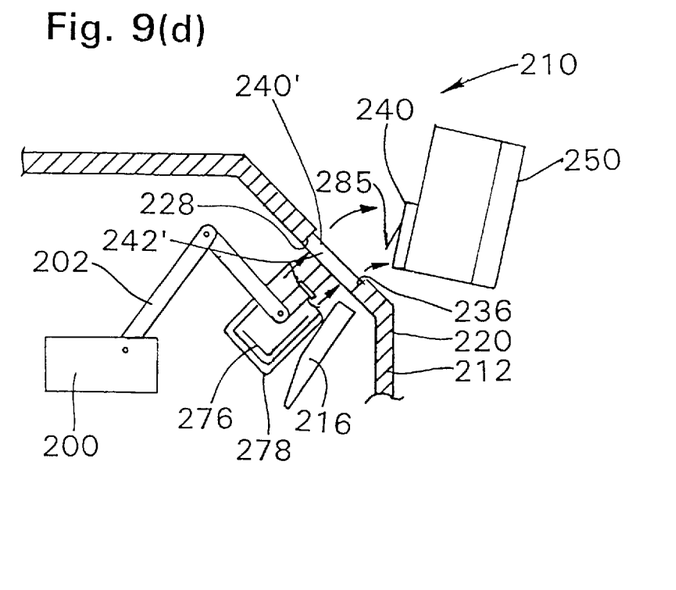
Figure 9E:
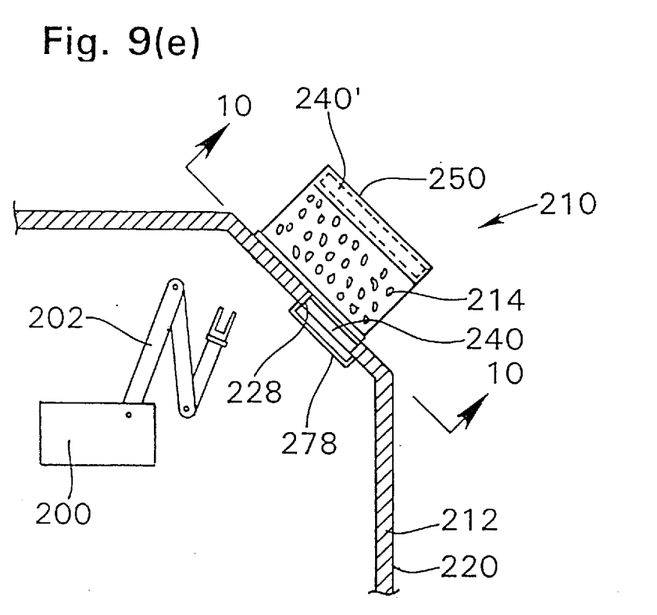
Figure 10:
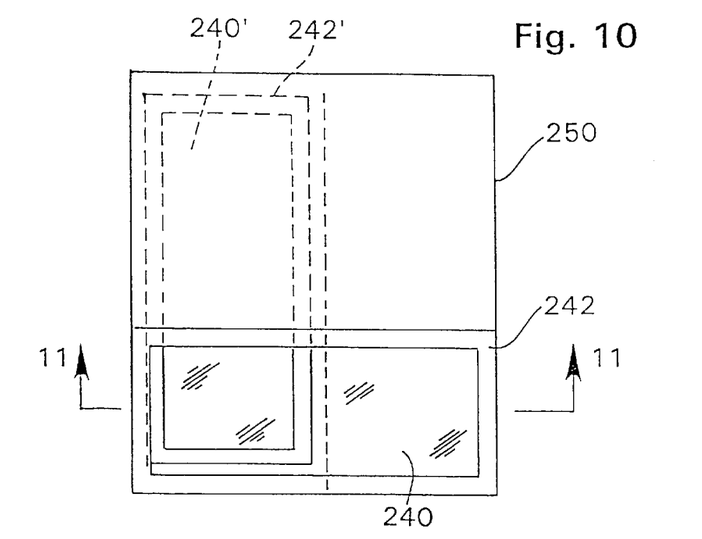
FIG. 10 is a view of the container and the attached port barrier film in accordance with the third embodiment of the invention taken along lines 10—10 in FIG. 9(e)
Figure 11:
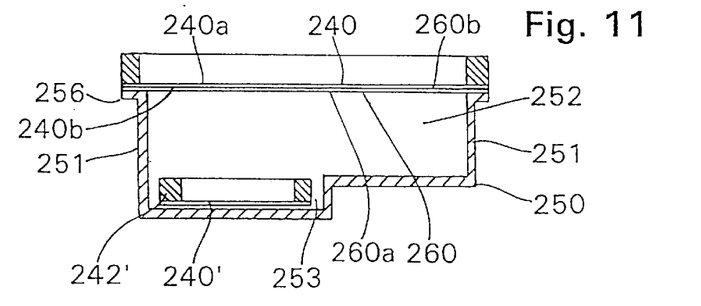
FIG. 11 is a cross-sectional view of the container and port barrier film in accordance with the third embodiment of the invention taken along lines 11—11 in FIG. 10.
Figure 12:
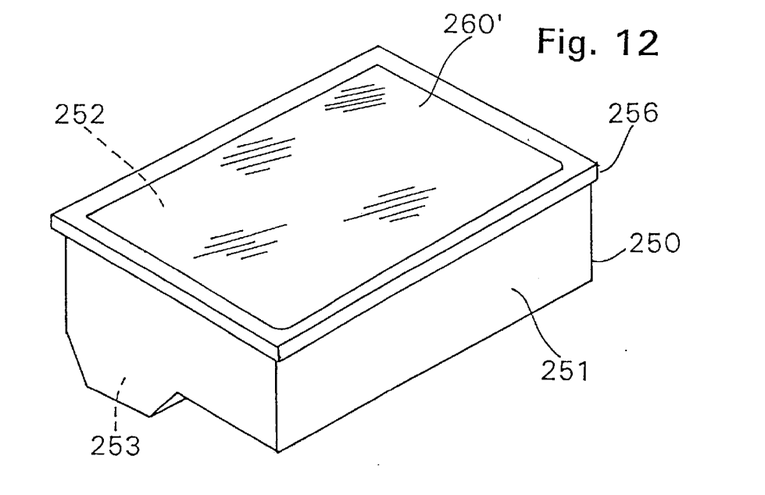
FIG. 12 is a perspective view of the container in accordance with the third embodiment of the invention.

As shown in FIGS. 9(a)–9(e), and in detail in FIGS. 10–12, a container 250 having an interior cavity 252 is provided. A second port barrier film 240', which is also preferably mounted on a frame 242', is located in the container 250. Preferably, the frame 242' of the second replacement port barrier film 240' has an outer periphery which is complementary to the port opening 228 such that the second port barrier film 240' can be sealingly engaged by at least one annular seal 236 in the port opening 228 as it is slidably installed.

Referring to FIGS. 10–12, the container 250 is shown in detail. In FIGS. 10 and 11, the container 250 has been illustrated with the frame 240 and the port barrier film located against the container barrier film 260. Preferably the container 250 is formed from a plurality of walls 251 which define the interior cavity 252. The container includes a separate recessed area 253 opposite to the opening 255 for containing the second, replacement port barrier film 240'. Preferably, a flange 256 is provided around the opening 255 for sealingly attaching the container barrier film 260 to seal the opening 255 with the decontaminated objects and the second, replacement barrier film 240' in the interior cavity 252.

A container barrier film 260 is sealingly connected to the container 250, preferably on a container flange 256. However, it can be sealingly connected to the container 250 in any desired manner as long as the interior cavity 252 is sealed to maintain the decontaminated objects 214 and the second, replacement port barrier film 240' in a decontaminated state. The container barrier film 260 has a first, decontaminated side 260a which faces the cavity 252, and a second, exposed side 260b which is positionable adjacent to the first port barrier film 240. The container barrier film 260 and container opening may be limited to the size of the port barrier film 240, as shown in FIGS. 10 and 11, or may extend over a container opening which is larger than the port 228 as indicated by element number 260', shown in FIG. 12.

A parting and sealing element 276 is located within the isolated space 222, and is mounted for movement to an in-use position, as shown in FIG. 9(e), adjacent to the first port barrier film 240. Preferably, the parting and sealing element 276 is mounted on a door assembly 278. The parting and sealing element 276 is adapted to part the first port and container barrier films 240, 260 to define a transfer opening 280 therethrough having edges 282 in the first port and container barrier films 240, 260, and to simultaneously seal together and decontaminate the edges 282 of the first port and container barrier films 240, 260, in a similar manner to the first embodiment. The decontaminated objects 214 can then be passed into the isolated space 222 through the transfer opening 280 while maintaining the decontaminated environment, as shown in FIG. 9(a).

Referring to FIGS. 9(a)–9(e), the process for transferring objects 214 into the isolated space in accordance with the third preferred embodiment of the invention will be explained. First, a container 250 is placed adjacent to the port barrier film 240 on the port opening 228, with the container barrier film 260 being placed with its second exposed side 260b in facing engagement with the second exposed side 240b of the port barrier film, as shown in FIG. 9(e). The parting and sealing element 276 is then moved into position adjacent to the decontaminated side 240a of the port barrier film 240, and activated to simultaneously create the transfer opening 280 in the first port and container barrier films 240, 260, and seal the edges 282 formed around the transfer opening 280 in the first port and container barrier films 240, 260 together. The decontaminated objects 214 are then passed into the isolated space 222, as shown in FIG. 9(a).

The frame 242' with the second replacement port barrier film 240' is then removed from the compartment 253 in the container 250 utilizing a robotic arm 302 of a robot 300. The robotic arm 302 reaches through the transfer opening 280 after the objects 214 have been emptied from the container 250, as shown in FIG. 9(b). The frame 242' with the second replacement barrier film 240' is oriented such that its short side is aligned with the transfer opening 280 so it can be carried into the isolated space 222.

As shown in FIG. 9(c), the robotic arm 302 then rotates the frame 242' with the second replacement port barrier film 240' to the proper orientation such that it can be aligned with the port opening 228 and inserted. As the frame 242' is inserted into the port opening 228, the annular seals 236 sealingly engage the sides of the frame 242'. As shown in FIG. 9(d), the continued insertion of the frame 242' with the second replacement port barrier film 240' forces the first frame 240 with the first port barrier film 240, which is now attached to the container barrier film 260, out of the port opening 228. This results in the configuration shown in FIG. 9(e), with the port barrier film 240' now being in position in the port opening 228 such that a next container 250 of objects to be delivered into the isolated space 222 can be placed in position and the process repeated. This provides additional advantages over the first preferred embodiment because a new replacement port barrier film is delivered with each new container 250 of objects 214.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A transfer system for transferring objects into a barrier isolator which includes a barrier wall to maintain a decontaminated environment in an isolated space, the transfer system comprising:

a port opening located in the barrier wall to provide access to the isolated space;

a first port barrier film sealingly located over the port opening, the first port barrier film having a first, decontaminated side which faces the isolated space and a second side which faces away from the isolated space;

a container having an interior cavity which contains a second, replacement port barrier film and which is adapted to further receive and hold decontaminated objects to be delivered through the port opening and into the isolated space;

a container barrier film sealingly connected to the container to maintain the decontaminated objects and the second, replacement port barrier film within the cavity in a decontaminated state, the container barrier film having a first, decontaminated side which faces the cavity, and a second exposed side, positionable adjacent to the port barrier film;

a parting and sealing element located within the isolated space adjacent to the port opening, pivotably mounted for movement from a first, inoperative position out of alignment with the port opening to a second in-use position adjacent to the first side of the first port barrier film, where the parting and sealing element is adapted to part the first port barrier film and the container barrier film to define a transfer opening having edges in the first port barrier film and the container barrier film and to simultaneously seal together and decontaminate the edges of the first port barrier film and the container barrier film such that the exposed and potentially contaminated second sides of the first port barrier film and the container barrier film are locked together and remain isolated from the isolated space, whereby the decontaminated objects and the second, replacement port barrier film can be passed from the container cavity, through the transfer opening and into the isolated space while maintaining the decontaminated environment.

2. The transfer system of claim 1 further comprising a holder located adjacent to the port opening and adapted to position the container against the port opening with the second side of the first port barrier film in facing engagement with the second side of the container barrier film.

3. The transfer system of claim 1 further comprising a surface surrounding the port opening in the barrier wall, the surface having a depth, and a plurality of spaced apart, annular seals being located on the surface, the first port barrier film being mounted in a first frame having an outer periphery which is complementary to the port opening, the second, replacement port barrier film being mounted in a second frame having an outer periphery which is complementary to the port opening, the outer periphery of the first and second frames being adapted to be sealingly engaged by at least one annular seal and being slidably displacable through the port opening.

4. The transfer system of claim 3 wherein the second frame is located within the container with the second, replacement barrier film.

5. The transfer system of claim 3 wherein the first and second frames each have a thickness, and the depth of the surface is greater than the combined thicknesses of the first and second frames such that the first frame with an associated container connected by the parted and sealed barrier films can be displaced outwardly from the port opening while the second frame is sealingly engaged by at least one annular seal in the port opening to maintain isolation of the isolated space as the first frame is removed.

6. The transfer system of claim 1 further comprising a robotic arm located within the isolated space, the robotic arm being adapted to remove the second, replacement port barrier film from the container and sealingly install the second, replacement port barrier film in the port opening prior to removal of the container with the first port barrier film.

7. The transfer system of claim 1 wherein the container includes a flange and the container barrier film is sealingly connected to the flange, and a shield is located between the container barrier film and the flange to prevent the parting and sealing element from acting on the flange.

8. The transfer system of claim 1 wherein the parting and sealing element extends only partially around the port opening, and is adopted to form a flap in the first port and container barrier films such that no loose pieces are created.

9. The transfer system of claim 8 wherein a flap support is located within the isolated space and is movable from a first position, which is adopted to hold the flap closed, to a second position, which is adopted to allow the flap to open.

10. The transfer system of claim 9 wherein the parting and sealing element and the flap support are located on a door assembly pivotably mounted within the isolated space.

11. A method of supplying decontaminated objects and a replacement port barrier film to a decontaminated environment in an isolated space delimited by a barrier wall, comprising the steps of:

(a) providing a port opening in the barrier wall and a first port barrier film sealing the port opening, the first port barrier film having a first, decontaminated side facing the isolated space to close-off the isolated space and a second exposed side;

(b) positioning a container adjacent to the port opening, the container having a decontaminated interior cavity with decontaminated objects and a second, replacement port barrier film sealed within the cavity b a container barrier film, the container barrier film having a first decontaminated side and a second, exposed side, the second side of the first port barrier film being in facing engagement with the second side of the container barrier film;

(c) moving a pivotably mounted parting and sealing element pivotably from a first, inoperative position out of alignment with the port opening to a second, in-use position and simultaneously creating a transfer opening in the first port barrier film and the container barrier film and sealing together edges formed around the transfer opening in the first port barrier film and the container barrier film with the parting and sealing element;

(d) transferring the decontaminated objects and the second, replacement port barrier film from the container, through the transfer opening in the first port barrier film and the container barrier film, and into the isolated space; and (e) resealing the port opening with the second, replacement port barrier film while maintaining the decontaminated environment in the isolated space.

* * * * *